United States Patent [19]
Vainberg et al.

[11] Patent Number: 5,547,684
[45] Date of Patent: Aug. 20, 1996

[54] COSMETIC COMPOSITION CONTAINING A DNA-SODIUM SALT AND METHODS OF MAKING AND USING THE SAME

[75] Inventors: Yuri P. Vainberg; Elli N. Kaplina; Ideya G. Andosova, all of Moscow, Russian Federation

[73] Assignee: Pharmec Company, Moscow, Russian Federation

[21] Appl. No.: 16,014

[22] Filed: Feb. 10, 1993

(Under 37 CFR 1.47)

[51] Int. Cl.⁶ .......................... A61K 35/52; A61K 6/00; A61K 31/70
[52] U.S. Cl. .......................... 424/561; 424/401; 514/44; 514/844; 514/847; 514/848; 514/944
[58] Field of Search .................. 424/78.03, 520, 424/401, 486, 488, 561; 514/944, 844, 847, 848, 44

[56] References Cited

U.S. PATENT DOCUMENTS 5,194,253  3/1993  Garrido .............................. 424/78.03

*Primary Examiner*—John W. Rollins
*Attorney, Agent, or Firm*—Burgess, Ryan and Wayne

[57] ABSTRACT

Cosmetic preparations are provided containing a DNA-sodium salt and which are useful, for example, for the treatment of aging skin and skin problems.

7 Claims, No Drawings

COSMETIC COMPOSITION CONTAINING A DNA-SODIUM SALT AND METHODS OF MAKING AND USING THE SAME

FIELD OF THE INVENTION

This invention is directed to pharmaceutical compositions containing DNA-sodium salts which stimulate the productions of white blood cells, lymphocytes and neutrophils in the peripheral blood system and therefore are useful in the treatment of various diseases. In one aspect, the invention is directed to certain metal complexes of DNA-sodium salts having antiviral activity. In another aspect the invention relates to cosmetic formulations containing DNA-sodium salts. In a further aspect, the present invention relates to an improved method of obtaining DNA-sodium salts from natural sources.

BACKGROUND OF THE INVENTION

Over the years, a wide variety of compounds which exhibit desirable biological properties have been obtained from plants and animal sources. Upon identification of the chemical structure of the active ingredient(s), it was possible, in many cases, to synthesize the active component using known chemical techniques and therefore prepare the compounds in large quantities and at reasonable costs.

More recently, in a search for new bioactive materials, investigations have been directed to the components of the nucleus of cellular structures and methods for extracting and refining biologically active materials contained therein. Various studies have been reported in the literature of the extraction and refinement of genetic materials contained in both plants and animals, and a wide variety of microorganisms. Methods have been developed for extracting genetic materials from cells for further study and modifications through genetic engineering techniques.

Medical researchers, biologists, chemists and other scientists are continually searching for, and evaluating new sources of materials in the hope of finding compounds which possess unexpected and useful properties which might make them useful in the treatment of various diseases. The present invention is therefore directed to the extraction, refinement and use of biological materials possessing most desirable characteristics for use in the pharmaceutical field.

Prior to the present invention, it had been known that a high polymer DNA could be obtained from sturgeon soft roe by extraction of the DNA with sodium pyrophosphate. Additionally, methods have been disclosed for obtaining a sterile sodium DNA salt from aquatic animal sources.

The invention is therefore directed to an improved method by which DNA products could be obtained in relatively high yields from aquatic animals, such as sturgeon by a process which avoids the use of excessive amounts of solvent such as ethanol. Additionally, it was desired to provide new DNA sodium salts having improved properties and greater potency than the DNA sodium salt obtained by prior art methods.

Accordingly, one or more of the following objects will be achieved by the practice of this invention. It is an object of this invention to provide a composition in biologically pure form, which is capable of stimulating the production of white blood cells in a warm-blooded animal. Another object of the invention is to provide a composition which can also stimulate the production of lymphocytes and neutrophils in the peripheral blood system of a warm-blooded animal. A further object is to provide a novel composition which is useful in the treatment of various diseases. Another object is to provide certain metal complexes of the composition which have antiviral activity. A further object is to provide cosmetic formulations which contain DNA-sodium salts. A still further object is to provide an improved process for the extraction of a native DNA salt from animal cells in relatively high yields and without the use of large quantities of solvents. These and other objects will readily become apparent to those skilled in the art in light of the teachings herein set forth.

SUMMARY OF THE INVENTION

The present invention relates in general to novel, highly pure DNA-sodium salts which stimulate the production of white blood cells, lymphocytes and neutrophils and their use in the treatment of a variety of diseases. The DNA-sodium salts are also useful in cosmetic formulations. The invention is also directed to certain metal complexes of these DNA salts and to an improved method for the production of bioactive materials, and particularly to the preparation of novel DNA-sodium salts.

The DNA-sodium salt products of the present invention, hereinafter also referred to as "NPD" can also be used in the form a pharmaceutical compositions for the treatment of (a) the side effects from the administration of chemo and/or radiation therapy; (b) irregularities of the surfaces of various organs (i.e., throat, stomach, intestine and the like); (c) vascular diseases such as phlebitis and hemorrhoids; (d) diabetes mellitus; (e) burns, particularly those due to overexposure to radiation; (f) external wounds; and (g) chronic viral conditions including those caused by the HIV and related viruses. The compositions can be administered in a variety of forms including intranasal, intramuscular and as topical compositions. In addition, the compositions of the present invention can be used as a cosmetic especially for the rejuvenation of aging skin.

DETAILED DESCRIPTION OF THE INVENTION

The DNA-sodium salts of the present invention are obtained from naturally-occurring sources such as animal sources, and in particular from the reproduction cells of certain aquatic animals such as sturgeon milt. Although the milt from seruga or beluga can also be used, in other types of fish, the DNA structure and compositions are sufficiently different so as to render them undesirable for the same utilities described above.

The active ingredient of the compositions can be prepared by a process comprising:

(1) homogenizing the sturgeon milt in an aqueous solution of sodium chloride and sodium citrate to provide a homogenized material;

(2) washing said homogenized material with an aqueous solution of sodium chloride and sodium citrate;

(3) contacting said washed material in a reaction chamber with:
   (a) an aqueous solution of sodium chloride and sodium citrate,
   (b) a detergent, and
   (c) an aqueous sodium chloride solution;

(4) separating and concentrating a liquid fraction containing the bioactive material;

(5) washing said concentrated liquid fraction until a negative protein reaction is indicated in the permeate; and (6) thereafter, recovering a refined bioactive material as the DNA-sodium salt.

As indicated, the process is generally conducted beginning with the homogenization of the milt material after it has been obtained from the fish and cleansed. Homogenization is conducted in an aqueous solution of sodium chloride and sodium citrate. In practice, the solution contains from about 0.01M to about 0.8M, preferably from about 0.05M to about 0.2M of sodium chloride and from about 0.005M to about 0.05M of sodium citrate. From about 10 grams to about 150 grams of the starting material (milt) will be homogenized in about 20 to about 2000 milliliters of the aqueous solution. Homogenization is effected from about 3 seconds to about 20 minutes at a temperature of from about 4° C. to about 40° C.

In the second step, the homogenized material is washed from about 1 to about 7 times with the same volume of sodium chloride-sodium citrate solution. Thereafter, in the third step, the washed material is placed in an enamel reaction chamber equipped with a heating/cooling jacket and a rotor mixer, and containing the following additional components:

(a) from about 0.01M to about 0.9M of the sodium chloride-sodium citrate solution, (b) from about 0.1% to about 6% by weight of a detergent, and (c) from about 1M to about 3M of an aqueous sodium chloride solution.

Cell and nuclear membrane lysis, protein separation from DNA, protein denaturing and protein-sediment formation take place in the reaction chamber in the third step.

The temperature in the chamber will usually be within the range of from about 10° to about 80° C., and the reaction time will usually be from about 3 to about 24 hours.

In the fourth step, the liquid fraction of the bioactive material, the DNA-sodium salt, is separation from the reaction mass by centrifugating or by filtration. The liquid fraction can, if desired, be processed by ultrasound at about a 22 kHz frequency for about 15–20 minutes at an intensity of about 10–12 W/cm. Finally, after the first and sixth steps, the material is further washed until a negative protein reaction is indicated and the DNA-salt recovered.

The bioactive DNA-salt material obtained by the above process is characterized by the following properties. It is a white powder containing not less than about 80% by weight of native DNA-sodium salt extracted from the sturgeon milt, not more than about 1% by weight of proteins, not more than about 17% by weight moisture, and the remainder sodium chloride.

The nucleotide composition of the DNA extracted from sturgeon milt is as follows:

| Nucleotide | Mole Percent |
| --- | --- |
| Adenine | 29.0 ± 0.9 |
| Thymine | 27.0 ± 0.9 |
| Guanine | 22.0 ± 0.9 |
| Cytosine | 20.0 ± 0.9 |

The native DNA sodium salt has a molecular weight of about $270-500 \times 10^3$ daltons and a hyperchromicity effect (G): G 37%.

Hyprochromicity is determined from the difference in absorption spectrum of denatured and native preparation solutions at wave length of 260 nm.

0.15 g of the preparation (precise measurement) is placed into a measured 25 ml retort, 0.1% sodium chloride solution is added, the preparation is dissolved and the volume is brought up to the mark (Solution 1). 1 ml of the received Solution 1 is placed into a measured 200 ml retort, the volume is brought up to the mark with 0.1% sodium chloride solution. Absorption of the received solution ($D_{260}$) is measured.

5 ml of Solution 1 is placed into a retort with thin section, 5 ml of 10% chloric acid solution, Closed and boiled on a water bath for 20 min. The solution is cooled own to the normal temperature, transferred by quantity into a measured 100 ml retort, the volume is brought up to the mark with water. 5 ml of this solution is placed into a measured 50 ml retort and the solution volume is brought up to the mark with water. Absorption of the received solution ($D^1_{260}$) is measured.

Hypochromicity is calculated according to the following formula:

$$H\% = \frac{D^1_{260} - D_{260}}{D^1_{260}} \times 100, \text{ where}$$

H %–hypochromicity in %, $D_{260}$—native preparation solution absorption, $D^1_{260}$—denatured preparation solution absorption.

As indicated above, the process for preparing a DNA-sodium salt utilizes a detergent in step (3). Preferred are the sodium salt detergents and include sodium dodecyl (lauryl/sulfate, sodium xilosulfonate, sodium acetotri-hydrate, sodium benzoate and the like.

Sodium salts of other strong acids can be used instead of NaCl, for example, sodium sulphate, sodium phosphate, sodium phenylphosphate, and the like.

Sodium salts of other weak acids can be used instead of sodium citrate, for example, sodium acetate, ethylenediaminetetraacetic acid disodium salt and the like.

In other embodiments as hereinafter indicated, the DNA sodium salt obtain by the aforementioned process can also be complexed with certain water-soluble metal salts or it can be used in cosmetic formulations.

The DNA-sodium salts obtained in accordance with the present invention can be formulated into pharmaceutical compositions comprised of the active component and one or more suitable pharmaceutically acceptable carriers. Although a variety of pharmaceutical compositions can be prepared, it has been found that only solutions of sodium chloride can be used for dissolving the DNA. Other salts were observed to alter the characteristics of the compositions.

In practice, pharmaceutical compositions prepared in accordance with the present invention will have a concentration of sodium chloride within the range of from about 0.1 percent to about 0.9 percent by weight. At salt concentration below about 0.1 percent, the native DNA sodium salt is destroyed while at concentrations higher than about 0.9 percent by weight, it is not only difficult to filter the DNA-containing solution but treatment can cause complications.

Although pharmaceutical compositions can be prepared containing different concentrations of native DNA sodium salts, three typical formulations have been prepared and evaluated. The formulations have the following designations and composition by weight.

NPD-A Sterile 1.5 percent solution of NPD in a 0.1 percent aqueous solution of NaCl and stored in 5 ml aliquots.

NPD-B Sterile 0.25 percent solution of NPD in a 0.1 percent aqueous solution of NaCl and stored in 10 and 20 ml aliquots.

NPD-C Sterile 0.25 percent solution of NPD in a 0.1 percent aqueous solution of NaCl and stored in 40 ml aliquots.

The concentration of the native DNA sodium salt in the pharmaceutical compositions can range up to about 4 percent by weight. However, at this concentration, the solutions become very viscous and almost gel-like—the preferred concentration is from about 0.1 to about 4 percent by weight based on the total weight of the pharmaceutical composition for formulations NPD-B and NPD-C and from about 0.2 to about 4 percent for formulation NDP-A. Particularly preferred compositions contain from about 0.1 to about 2.5 percent.

If desired, other ingredients can be included with the DNA sodium salts in the pharmaceutical compositions of this invention. Both inert and active ingredients can be employed as long as they do not adversely react with or adversely effect the main active component.

The pharmaceutical preparations of the present invention can be formulated for administering the active component to a patient by injection, intranasally or topically in a suitable cream type composition.

Injectable NPD-A and intranasal NDP-B are useful for the treatment of side effects of chemotherapy and radiation therapy. An injection of 5 ml of the NPD-A formulation is given within 2–15 days after therapy. Alternatively, 5 ml portions of NPD-B may be used as a mouth cavity gargle 6 to 8 times a day for 3 to 4 days.

For the treatment of vascular diseases, only the intranasal formulation is used. 2 drops of NPD-B are placed into each nostril 4–10 times a day for 30 days.

The following examples are illustrative of this embodiment of the invention:

EXAMPLE 1

1 kg of frozen sturgeon milt is cut to fragments and homogenized in 2 liter of citrate-salt solution consisting of 0.15M of sodium chloride and 0.0021M of sodium citrate at normal temperature. The obtained homogenate is then poured into the reactor, in which 34 liters of citrate-salt solution is already found. Then 4 liters of 6% sodium dodecylsulphate solution in 45% solution of pure ethanol (240 grams in 4 liters of 45% ethanol). The obtained mass is warmed up to 60°–65° C. within 1–1.5 hours and stirred by a rotor mixer for 1.5 hours. Then 40 liters of 5M NaCl solution are added and the mixture is stirred for another 1.5 hours. Then the resulting mass is cooled to 12°–16° C. and processed by ultrasound at the frequency of 22 kHz for 45 minutes with the intensity of 10–12 W/cm$^2$. The liquid fraction is concentrated by ultrafiltration method in columns with hollow fibers, NaCl, water and water-soluble low polymer protein go to the permeate, DNA-Na remains in the liquid fraction which is then concentrated up to 6% of DNA-Na, that is 6 or 7 times. After that the concentrate is washed with the help of diafiltration until negative reaction for water-soluble protein is obtained in the permeate. As a result, approximately 10–12 liters of native DNA-Na sodium salt 6–7% solution are obtained, with the DNA-Na possessing the following characteristics:

Molecular weight: 0.3–0.5 MD;

Protein: not more than 1.0% by weight

Hypochromicity: not less than 87%

The concentrate containing 6–7% of native DNA sodium salt is processed by 96% rectified ethanol (1:1). The sediment is separated and washed, first by 70% ethanol aqueous solution from NaCl, then by 96% ethanol from moisture, then dried in a special drying chamber at the temperature of 40° C.

EXAMPLE 2

Preparation of an Injectable Composition Containing NPD

An injectable formulation containing the DNA sodium salt of the present invention was prepared by dissolving 1 gram of sodium chloride in 1 liter of bidistilled non-pyrogenic water at room temperature (25° C.). 311.25 grams of NPD powder were added to the solution and dissolved by stirring for 3 hours at room temperature. The resulting solution was filtered through a system of consecutive membrane filters of 0.8 microns, 0.65 microns, 0.45 microncs and 0.22 microns. The filtrate obtained from the last filter was transferred into sterile, glass containing in 10 or 20 ml aliquots, closed, sealed and labelled.

EXAMPLE 3

Preparation of an Intranasal Composition Containing NPD

A pharmaceutical composition which is useful for the intranasal administration of the DNA sodium salt to a patient is prepared by dissolving 1 gram of sodium chloride in 1 liter of bidistilled non-pyrogenic water at room temperature (25° C.). 31.25 grams of NPD powder were added to the solution and dissolved by stirring for 1.5 hours at room temperature. The resulting solution was filtered through a system of consecutive membrane filters of 0.8 microns, 0.65 microns, 0.45 microns and 0.22 microns. The filtrate obtained from the last filter was transferred into sterile, glass containers in 10 or 20 ml aliquots, closed, sealed and labelled.

In the following example, the pharmaceutical compositions of the present invention were used for the treatment of side effects of chemotherapy and radiation therapy in male and female children ranging in age from 5 to 15 years and afflicted with tumors. Treatment was administered at the National Oncology Center of the USSR Academy of Medical Sciences and involved chemotherapy or radiation therapy. Blood analysis before therapy, after therapy and after treatment with the composition of this invention are set forth. In many cases, the patient had received earlier treatment at their local hospital for their conditions before being admitted to the National Oncology Center.

EXAMPLE 4

A female child, weight 20 kg, height 122 cm, 7 years old, was diagnosed as having left nephroblastoma.

Treatment:

08.16.91–08.20.91: an aggressive polychemotherapy course was administered:

1. vepesid i/v by 80 mg N5

2. cyclophosphan i/v by 250 mg N5

3. platidiam i/v by 16 mg N5.

The patient endured the treatment well, vomiting occurred within the first two days of the cycle.

X-ray 08.22.91: Favorable dynamics expressed by a decrease in the tumor focus size to 7.5%–9 cm.

Blood analysis 08.20.91: leucocytes—4,100

08.23.91: transferred to the rehabilitation department, received courses of general supporting and symptomatic therapy.

08.26.91: leucocytes—2,600

Blood analysis 08.30.91:

leucocytes—1,200 hemoglobin—9.0 erythrocytes—2,700

ESR—10 thrombocytes—20%–64,000

08.30.91: 12.0 ml of NPD-A solution administered subcutaneously.

Blood analysis 09.02.91: leucocytes—2,800

Blood analysis 09.05.91:

leucocytes—3,200 hemoglobin—10.8 erythrocytes—3,200,000

ESR—3 thrombocytes—25%–80,000

Blood analysis 09.09.91:

leucocytes—7,000 thrombocytes—60%–138,000 hemoglobin—8.5 erythrocytes—2,300,000

The child was discharged for an interval after the treatment course.

EXAMPLE 5

A female child, 11 years old, weight 29.5 kg, height 13 cm was diagnosed as having accessory skull sinuses tumor. She had been operated on prior to admission to the Oncology Center.

Treatment:

07.09.91–07.12.91

08.01.91–08.04.91: two courses of polychemotherapy were administered along the following scheme:

|  | 1 day | 2 day | 3 day | 4 day |
|---|---|---|---|---|
| vinkristin (mg) i/v | 1.5 | 0.5 | 0.5 | 0.5 |
| adriamycin (mg) i/v |  | 30 | 30 |  |
| cyclophosphan (mg) i/v | 600 |  |  |  |
| platidiam (mg) i/a |  |  |  | 60 |

Lumber punctures were made twice in the course of treatment: no blastic cells detected.

08.26.91: upon control examination in the Polyclinic or Scientific and Research Institute of Pediatric Oncology:

Blood analysis: leucocytes—4,600;

Another course of polychemotherapy began:

vincristine 1.5 mg i/v—08.26.91 cyclophosphan 600 mg i/v—08.26.91 vincristine 0.5 mg i/v—08.27.91 farmarubicin 30 mg i/v—08.27.91

Blood analysis 08.28.91: leucocytes—1,600

PCT course aborted; the child was transferred to the rehabilitation department.

08.30.91: 15.0 ml of NPD-A solution administered subcutaneously

Blood analysis 09.02.91: leucocytes—2,800

Blood analysis 09.04.91:

leucocytes—3,400 hemoglobin—13.2 erythrocytes—4,160,000

ESR—2 thrombocytes—40%–166,400

Blood count:

basophils—2 eosinophils—6 juvenile neutrophils—1 stab neutrophils—2 segmented neutrophils—46 lymphocytes—34 monocytes—9

Blood analysis 09.09.91:

leucocytes—3,500 hemoglobin—11.6 erythrocytes—3,430,000

ESR—3 thrombocytes—45%–154,350

Blood count:

eosinophils—7 stab neutrophils—2 segmented neutrophils—39 lymphocytes—38 monocytes—14

09.10.91: the girl was transferred to the NOC Clinic for treatment continuation.

EXAMPLE 6

Male child 5 years old. Weight 18 kg, height 112 cm was diagnosed as having acute lymphoblastic leucosis 2.

Treatment:

Since 05.14.90: a PCT course along the following scheme:

1. prednisolone—40 mg daily 2. vincristine—i/v, 5 by 1.0 mg 3. methotrexate—endolumbarly, 4 by 7.5 mg 4. rubomycin—i/v, 1 by 20 mg;

Myelogram 05.30.90: blastic cells—1.0%

Blood analysis 06.18.90:

leucocytes—5100

ESR—2 erythrocytes—3,000,000 hemoglobin—9.4 thrombocytes—240,000

Blood count:

segmented neutrophils—64 lymphocytes—33 monocytes—3

Since 07.23.90: a PCT course (remission consolidation) along the following scheme:

1. prednisolone—40 mg daily 2. cytosar—5 by 70 mg

3. L-asparaginase—6 by 15.000 units 4. methotrexate—3 enlarged doses (300,700 and 500 mg)

After the PCT course radiation treatment was administered for neuroleucosis prophylactic, total dosage 24 Gray; the patient endured the treatment well;

Myelogram 09.12.90: 1.0% of blastic cells;
Discharged for off-hospital supporting therapy.
10.24.91: admitted to the NOC children's rehabilitation department for a PCT course, upon admission—2000 leucocytes in the blood analysis.
10.25.91: 12.0 ml of NPD-A solution administered intramuscularly.
Blood analysis 10.28.91
leucocytes—2700
Blood analysis 10.30.91:
leucocytes—4200
ESR—3
erythrocytes—4,320,000
hemoglobin—12.5
thrombocytes—35%–150,000
Blood count:
eosinophils—1
stab neutrophils—1
segmented neutrophils—62
lymphocytes—21
monocytes—16;

EXAMPLE 7

A female child 13 years old, weight 34 kg, height 157 cm, diagnosed as having Ewing's sarcoma.
Treatment:
10.19.91–10.24.91: a PCT course along the following scheme:

|  | day 1 | day 2 | day 3 | day 4 |
|---|---|---|---|---|
| vinkristin mg i/v | 1.8 | | | |
| adriamycin, mg (i/v) | 60 | | | |
| cyclophosphan, mg i/v | | 1400 | | |
| platidiam, mg (i/a) | | | | 100 |

Blood analysis 10.23.91:
leucocytes—3100
ESR—24
erythrocytes—4,380
hemoglobin—13.2
thrombocytes—80%–301,000
Blood count:

stab neutrophils—6
segmented neutrophils—76
lymphocytes—14
monocytes—4;

10.28.91: transferred to the children's rehabilitation department.
Blood analysis 10.31.91:
leucocytes—1200
erythrocytes—11
hemoglobin—13.2
thrombocytes—60%–288,000
Blood count:
segmented—5
lymphocytes—14
monocytes—6 (calculated for 25 cells);
10.31.91: 15.0 ml of NPD-A solution as administered intramuscularly.
Blood analysis 11.02.91:
leucocytes—1700;
Blood analysis 11.04.91:
leucocytes—3100
ESR—5
erythrocytes—4,880
hemoglobin—14.1
thrombocytes—50%–244,000
Blood count:
basophils—1
eosinophils—3
stab neutrophils—2
segmented neutrophils—13
segmented neutrophils—61
monocytes 20;
Blood analysis 11.12.91:
leucocytes—5000;
11.13.91: transferred to the NOC Pediatric Oncology Department for treatment continuation.

EXAMPLE 8

A female child, 15 years old, weight 56 kg, height 169 cm was diagnosed as having lymphogranulomatosis, primary lesion of servico-supraclavicular lymph nodes on both sides and mediastinum. She had 5 previous PCT courses administered (adriamycin included in the third one) at the National Oncology Center.
Treatment:
Since 01.01.91 the girl was transferred in the children's rehabilitation department where she received PCT along the following scheme:

|  | d. 1 | d. 2 | d. 3 | d. 4 | d. 5 | d. 6 | d. 7 | d. 8 | d. 9 | d. 10 | d. 11–14 | d. 15 |
|---|---|---|---|---|---|---|---|---|---|---|---|---|
| prednisalon mg (orally) | 60 mg daily throughout the whole cycle | | | | | | | | | | | |
| cyclophosphan, mg (i/v) | 950 | | | | | | | | 950 | | | |
| vinblastin mg (i/v) | 9.5 | | | | | | | | 9.5 | | | |
| natulan, mg (orally) | 50 | 100 | 150 | 150 | 150 | 150 | 150 | 150 | 150 | 150 | by 200 | |
| pharmarubycin, mg (i/v) | | | | | | | | | 60 | | | 60 |

Blood analysis 10.08.91:
leucocytes—3300
Blood analysis 10.11.91:
leucocytes—3500
ESR—2 erythrocytes—3,630 hemoglobin—14.2 thrombocytes—70%–252,000

Blood analysis 10.15.91:

leucocytes—1500

10.15.91:12.0 ml of NPD-A solution administered intramuscularly.

Blood analysis 10.16.91:

leucocytes—1800

Blood analysis 10.18.91 leucocytes—3700

Blood analysis 10.25.91:

leucocytes—7200

ESR—3 erythrocytes—3.760 hemoglobin—12.5 thrombocytes—70%–259,000

Blood count:

stab neutrophils—1 segmented neutrophils—86 lymphocytes—6 monocytes—7;

The girl was discharged in a satisfactory state, consultation in the NOC clinic was recommended in two months.

EXAMPLE 9

Intensive chemo and radiation therapy are presently used for treating hemoblastoses and malignant tumors. Such treatment generally results in lesions of the gastroenteric tract mucosal membranes found in 70–90% of the patients. This leads to problems of feeding up to complete anorexia, adds to the suffering of the patient and produces a noticeable negative influence upon the treatment results. The main disease process is complicated in this case by disbacteriosis, medication-induced stomatitis and secondary infections. Generally accepted methods of arresting emerging complications (oxicort, antiseptic solutions, antibiotic solutions, vitamins, antivirals, etc.) are, as a rule, ineffective.

0.25% NPD solution in 0.1% NaCl in 10 and 20 ml bottles was used for treatment.

481 patients suffering from lesions of the gastroenteric tract mucosal membranes resulting from extensive chemo and/or radiation therapy was treated in the following manner. All food fragments were removed from the mouth cavity. Each patient then rinsed their mouth cavity with 3–5 ml of a 0.25% DNA-sodium solution in 0.1% Nacl for 3–5 minutes with gradual swallowing of the solution with the saliva. The procedure was repeated from 6 to 10 times, depending on the graveness of the patient's state and local symptoms. Treatment was repeated as needed for up to one week. All patients regardless of the seriousness of the lesion showed a pronounced positive effect by the 2nd–4th day. Those having mouth cavity mucosal membrane expanded lesions exhibited a clear membrane almost completely by the 2nd day. In case of ulceronecrotic lesions, the patients allowed their mouth cavity to be examined in detail, were allowed to chew and swallow soft food, the mucosal membrane was fully cleared and epithelized on the 3rd–4th day. Those patients exhibiting colitis of the mouth cavity showed similar positive results.

In another embodiment of the present invention, various metal complexes were prepared with the DNA-sodium salt obtained from sturgeon milt and found to have high antiviral activity, and are therefore useful for the treatment of diseases particularly those caused by the HIV virus. The compounds which are particularly useful in the practice of this embodiment of the invention are the DNA-sodium salts which have been complexed with certain polyvalent metals. Suitable metals which can form complexes with the DNA-sodium salts of the present invention include magnesium, calcium, cobalt, nickel iron, zinc, selenium and gold. The metal is used in the form of water-soluble compound such as salts and bases. The complexes are obtained by mixing the DNA-sodium salt and the metal compounds dissolved in water at a temperature of from about 5° to about 40° C. and for a period of from about 5 minutes to about 2 hours. The preferred metals are zinc, nickel, cobalt and iron. The complexes can be prepared over a wide range of molar proportions of the DNA-sodium salt or polyvalent metal.

For example, the molar ratio of DNA-sodium to metal can range between 1:1 to 1000:1. These complexes of the DNA-sodium salt and the polyvalent metal have been given the designation AC and are identified as follows:

AC-1 for the Zm metal complex with Zn

AC-2 for the Ni metal complex with Ni

AC-3 for the Co metal complex with Co

AC-4 for the Fe metal complex with Fe

As indicated, the metal complexes were found to possess excellent antiviral properties.

The acquired human immunodeficiency syndrome (AIDS) has obtained world attention and much effort is being expended to inhibit the spread of this disease ad also to treat those who have become afflicted. When infected with the HIV virus, helper T-cells as well as others are destroyed leading to serious opportunistic infections and eventually death. No effective therapy for AIDS has been established except AZT which is a reverse transcriptase inhibitor and does provide some improvement in clinical symptoms. However, AZT is relatively toxic and in many instances causes adverse reactions.

Today AZT is known as the most popular antiviral preparation revealing in vitro high activity against retroviruses, HIV among them. AZT is used for supporting therapy at early stages of HIV infecting as well as the deep stage of HIV illness, AIDS. This preparation as indicated, is characterized by insufficient efficacy and high toxicity. AZT fails to completely stop the development of HIV in in vitro systems while optimal does of this preparation kill about 30% of normal cells. For cells, the AZT $LD_{50}$ does not exceed 0.1M, 10mg/kg of AZT injected intercerebrally to mice causes death of 50% of animals.

The objective of this embodiment of the invention was to create a less toxic antiviral agent revealing a stronger antiviral effect against HIV. This objective was achieved by producing a highly active preparation by complexing a DNA sodium salt (DNA-NA) with polyvalent metals as previously indicated. The complex, when introduced into the organism, penetrates, by means of endocytosis, into the cytoplasm of an actively fissing cell, lymphocyte, for example, binding both the reverse transcriptase (by forming connections through the metals constituting the complex) and HIV proteins produced by the infected cell genome (through interaction with the DNA part of the complex). The new stable triple complexes are, under the influence of intracellular ferments, gradually destroyed into separate fragments lacking anti-HIV activeness, and then utilized. As a result of these processes the development of HIV in the cell is inhibited by practically 100%. Thus, the characteristic feature of the antiviral preparation is its high anti-HIV activeness and low toxicity.

EXAMPLE 10

Complexes of DNA-Na with zinc, cobalt, nickel and iron were used for HIV suppression in in vitro systems with various concentrations of the components in the complexes. AZT manufactured by "Wellcome" Company was used for comparison purposes. The antiviral activity of the preparation was tested according to the method recommended by WHPO for these purposes. CEM-SS and MT-4 reinoculated human cell lines were used. The cells were cultivated in the concentration of $(0.03-0.05)*10^6$ cells per 1 ml of RPMI 1640 medium with 10% calf fetal serum, 300 mg/ml of L-glutamine, 100 mcg/ml of gentamicin and grown in the form of a suspension. The vitality of cells was tested by dyeing them with 0.4% solution of threpane blue dye stuff. HIV-IVS and HIV-1 HTLV/IIIB strains were used as the virus sources.

The cell suspension was placed into 24 well panels, processed by various doses of preparations and then infected by HIV. The infection multiplicity was 0.01 $TCD_{50}$ per cell. After that, the cultures were incubated at 37° C. in a 5% $CO_2$ atmosphere and 98% humidity for 5–7 days up to the moment of defining the cytopathic effect of the virus upon the cell culture.

Immunophermentative analysis was used to define formation of viral antigen.

The results are listed in Table 1.

2 and 3, that these materials have unexpected properties which render them useful in the treatment of AIDS.

EXAMPLE 11

Antiviral activity of these preparations toward HIV-1 was studied using as the model, cellular cultures infected with HIV-1.

The testing of anti-virus activity was conducted using two types of interwoven cellar lines sensitive to infecting by AIDS-virus—the MT-4 cells and Yurkat tat III cells. The cells were harvested in suspension form in a PPMI 1640 medium containing 15% of fetal serum with exposure to the atmosphere characterized by 5% $CO_2$ content, 98% humidity level and 37° C. temperature level. The cells were infected by the HTLV-IIIB culture of AIDS-1 virus in accordance with WHO recommendations for conducting scientific researches on testing pharmaceutical preparations. The methods used for determining anti-virus activity of the tested preparations are recommended for similar purposes by the WHO Reference Laboratory (Belgium) headed by Professor de Clerk who is an internationally recognized leading expert in synthesis and screening chemical preparations for AIDs treatment (I. Antimicrob. Chemoter., 1989, No. 23, Suppl. A 35–46). The work was done at the Virology Institute of the U.S.S.R. Academy of Medical Sciences on

ANTIVIRAL EFFECTIVE AND CYTOTOXICITY OF PREPARATIONS

| PREPARATION | DNA-Na Me M/M | QUANTITY OF SYNCITIA IN % FROM THE CONTROL VIRUS | IFA OPTICAL DENSITY | CYTOTOXICITY | | |
|---|---|---|---|---|---|---|
| | | | | ng/ml | QUANTITY OF CELLS IN ml OF CULTURAL LIQUID $\times 10^8$ | VITALITY OF CELLS % |
| DNA-Na | 4:9 | — | — | — | — | — |
| Zn | 3:10 | 25 | — | 0.25 | 0.83 | 69 |
| | 0.5:350 | 35 | — | 0.50 | 0.88 | 81.2 |
| | 1:1000 | 70 | 0.487 | — | 0.86 | 84.3 |
| | 1:1100 | 100 | 0.597 | — | 0.89 | 86.2 |
| DNA-Na | 4.9 | — | — | — | — | — |
| Ni | 3:10 | 0 | — | 0.1 | 0.82 | 71.0 |
| | 0.5:350 | 0 | — | >2.0 | 0.86 | 79.0 |
| | 1:1000 | 68 | — | >2.0 | 0.85 | 84.3 |
| | 1:1100 | 100 | 0.607 | — | 0.88 | 87.5 |
| DNA-Na | 4:10 | — | — | — | — | — |
| Co | 3:10 | 10 | 0.190 | — | 0.86 | 78.4 |
| | 0.5:350 | 15 | 0.184 | — | 0.84 | 87.1 |
| | 1:1000 | 66 | 0.414 | — | 0.89 | 76.3 |
| | 1:1100 | 100 | 0.585 | — | 0.87 | 82.1 |
| DNA-Na | 3:9 | — | — | — | — | — |
| Fe | 3:10 | 0 | 0.103 | — | 0.87 | 79.3 |
| | 0.5:350 | 0 | 0.247 | — | 0.84 | 82.1 |
| | 1:1000 | 61 | 0.492 | — | 0.87 | 81.7 |
| | 1:1100 | 100 | 0.595 | — | 0.85 | 84.5 |
| A T | | 8 | 0.091 | 0.1 | 0.61 | 55.2 |
| CONTROL VIRUS | | 100 | 0.602 | >2.0 | — | — |
| CONTROL CELLS | | 0 | 0.087 | <0.1 | 0.91 | 86.3 |

As is evident from the above table, DNA-Na complexes with zinc, cobalt, nickel and iron in a diverse spectrum of DNA/Me percentages (M/M) and exhibit high anti-HIV activeness while practically not revealing any cytotoxicity, an advantage over AZT.

In a further evaluation of the metal complexes of the DNA-sodium salt, applicants have evaluated preparations AC-1 and AC-4, obtained by the methods of this invention and found them to be highly active against AIDS in tests on cells and less toxic than "Retrovir" in tests on small laboratory animals. It is evident from the following methods used to evaluate the materials and the data set forth in Tables MT-4 human lymphoid cells and on Yurkat tat III cells as indicated above.

The cells were incubated for 6 days under similar conditions and thereafter their viability was determined as well as formation of virus-induced syncytia and virus antigen (p24) using immunofermental analysis. The formation of syncytia, huge cell conglomerates, is one of the HIV reproduction characteristics. The formation of the syncytia is connected with the interaction of gp120 virus protein, situated on the membranes of the infected cells, and CD4 receptor, situated on the membranes of non-infected cells. As a result of this interaction, the merging of nuclear membranes occurs and a cell culture lacking immune ability, consisting of many cells nuclei, is formed. The viable cells were counted using thripane blue dye-stuff in the Goryayev chamber. The error of the method in all cases does not exceed 5%.

The studies on toxicity of AC-1 and AC-4 and of aziodothymidine were conducted on non-linear white mice weighing 6 to 7 grams, making use of different concentrations of preparations per kg of weight of the animal in the volume of 0.2 ml in hypodermic, intranasal and intraabdominal injections and 0.03 ml in intracerebral injections. The animals were kept under observation for 2 weeks and then $LD_{50}$ was calculated using Curber method. The lethal dose of the preparation which has caused death of 50% of the animals was considered an $LD_{50}$ dose. The preparation was used as a sterile solution was a concentration of 0.05%.

Results: The results of the studies in anti-virus activities of these preparations are presented in Table 2 below:

TABLE 2

Determining anti-virus activity of AC-series preparations on cells (on the 6th day)

| preparation code | preparation dose mkg/ml | number of syncitia % | immunofermental activity ng/ml | viability % |
|---|---|---|---|---|
| AC-1 | 100 | 75 | 2.0 | 10 |
|  | 250 | 75 | 2.0 | 10 |
|  | 350 | 25 | 0.25 | 69 |
| AC-4 | 100 | none | 1.35 | 21 |
|  | 250 | none | 0.5 | 32 |
|  | 350 | none | 0.1 | 71 |
| AZT | 270 | none | 0.1 | 96 |

As evident from Table 2 above, the preparation AC-1, essentially, and the preparation AC-4, fully (in a dose of 350 mkg/ml) inhibits growth of HIV-1 virus similar to aziodothymidine. Additionally, the AC-4 preparation does not exhibit toxic effect upon cells.

Studies on toxicity of preparations on the model of laboratory animals (white mice):

Tests were conducted in parallel with 4 codified preparations in comparison with the preparation azidothymidine in doses of 5, 10, 20, 35 and 50 mg/kg. The studies on toxicity of the four preparation, namely AC-1, AC-2, AC-3, AC-4 and azidothymidine have been conducted on nonlinear white mice weighing 6 to 7 grams, making use of different concentrations of preparations per kg of weight of the animal in the volume of 0.2 ml in hypodermic, intranasal and intraabdominal injections and 0.03 ml in intracerebral injections. The animals were kept under observation for 2 weeks and then $LD_{50}$ was calculated using Curber method. The lethal dose of the preparation which caused death of 50% of the animal was considered the $LD_{50}$ dose.

The results of toxicity studies for these preparations are shown in Table 3.

TABLE 3

Estimating toxicality of preparations on white mice.

| NN nn | Preparation code | Method of introduction | Preparation dose mg/kg | | | | | |
|---|---|---|---|---|---|---|---|---|
| | | | 5 | 10 | 20 | 35 | 50 | 75 |
| 1. | AC-1 | in/cerebr. | 6/6 | 6/6 | 6/6 | 6/6 | 6/6 | 6/6 |
|  |  | hypoderm. | 6/6 | 6/6 | 6/6 | 6/6 | 6/6 | 6/6 |
|  |  | in/abdom. | 6/6 | 6/6 | 6/6 | 6/6 | 6/6 | 6/6 |
|  |  | in/nasal | 6/6 | 6/6 | 6/6 | 6/6 | 6/6 | 6/6 |
| 2. | AC-2 | in/cerebr. | 6/6 | 6/6 | 6/6 | 6/6 | 6/6 | 6/6 |
|  |  | hypoderm. | 6/6 | 6/6 | 6/6 | 6/6 | 6/6 | 6/6 |
|  |  | in/abdom. | 6/6 | 6/6 | 6/6 | 6/6 | 6/6 | 6/6 |
|  |  | in/nasal | 6/6 | 6/6 | 6/6 | 6/6 | 6/6 | 6/6 |
| 3. | AC-3 | in/cerebr. | 6/6 | 6/6 | 6/6 | 6/6 | 6/6 | 6/6 |
|  |  | hypoderm. | 6/6 | 6/6 | 6/6 | 6/6 | 6/6 | 6/6 |
|  |  | in/abdom. | 6/6 | 6/6 | 6/6 | 6/6 | 6/6 | 6/6 |
|  |  | in/nasal | 6/6 | 6/6 | 6/6 | 6/6 | 6/6 | 6/6 |
| 4. | AC-4 | in/cerebr. | 6/6 | 6/6 | 6/6 | 6/6 | 6/6 | 6/6 |
|  |  | hypoderm. | 6/6 | 6/6 | 6/6 | 6/6 | 6/6 | 6/6 |
|  |  | in/abdom. | 6/6 | 6/6 | 6/6 | 6/6 | 6/6 | 6/6 |
|  |  | in/nasal | 6/6 | 6/6 | 6/6 | 6/6 | 6/6 | 6/6 |
| 5. | AZT (azido thymidine) | in/cerebr. | 6/6 | 6/6 | 6/6 | 6/6 | 6/6 | 6/6 |
|  |  | hypoderm. | 6/6 | 6/6 | 6/6 | 6/6 | 6/6 | 6/6 |
|  |  | in/abdom. | 6/6 | 6/6 | 6/6 | 6/6 | 6/6 | 6/6 |
|  |  | in/nasal | 6/6 | 6/6 | 6/6 | 6/6 | 6/6 | 6/6 |
| 6. | Placebo | in/cerebr. | 6/6 | 6/6 | 6/6 | 6/6 | 6/6 | 6/6 |
|  |  | hypoderm. | 6/6 | 6/6 | 6/6 | 6/6 | 6/6 | 6/6 |
|  |  | in/abdom. | 6/6 | 6/6 | 6/6 | 6/6 | 6/6 | 6/6 |
|  |  | in/nasal | 6/6 | 6/6 | 6/6 | 6/6 | 6/6 | 6/6 |

NOTES:
numerator-the number of surviving mice
denominator-the number of infected mice.

It is evident from the Tables that all of the 5 preparations, no matter what their doses were, provided non-toxic for 6 to 7-gram white mice in hypodermic, intranasal and intraabodominal injections (2 weeks observation). However, 50% lethality in white mice has been registered when increasing 50 mg/kg dose of AC-4 preparation in intracerebral injections. The preparation azidothymidine also caused a 50% lethal rate in white mice when used in intracerebral injections in doses of 10 to 50 mg/kg per weight of the animal. So, the toxic effect of the azidothymidine preparation has been established for 6 to 7 gram white mice in intracerebral injections as $LD_{50}$ dose—10 mg/kg of weight.

The toxic effect of an AC-4 preparation using intracerebral injection of 5 mice has been recorded at the dose of 75, mg/kg of weight LD50 dose).

a) All the titres of the AC-series preparations proved non-toxic for 6 to 7 gram white mice in all injection methods at doses of 5 to 50 mg/kg of weight.

b) Azidothymidine was also non-toxic for white mice in all injection methods at doses of 5 to 50 mg/kg of weight except in intracerebral injections in doses of 10 to 50 mg/kg of weight.

c) Although the tested preparations showed lower antivirus activity in comparison with azidothymidine, nevertheless, AC-4 in a dose of 350 mkg/ml shows good anti-virus activity and no toxic effect on the tested cells. Hence, the $LD_{50}$ of AC-4 is at least 5 times that of AZT.

In summary, it was observed that:

1. Azidothymidine (AZT) in a dose of 1.0 mcm/ml completely suppresses the AIDS-1 virus development (virus-induced syncitia absent), the antigen (p24 content, as determined by immunofermental analysis technique, decreased from 2.0 ng/ml virus control down to 1 ng/ml.

2. AC-1 preparation in the same dose of 1.0 mcm/ml almost completely suppresses the AIDS-1 virus development (the amount of syncytia decreases from 100% of virus control to less than 25% of test suspension), the antigen content decreases from 2.0 ng/ml down to 0.25 ng/ml. Increasing the AC-1 preparation dose to 10.5 mcm/ml leads to a complete suppression of the AIDS-1 virus development according to the virus TITR test.

3. AC-4 preparation in a dose of 1.0 mcm/ml completely suppresses the AIDs-1 virus development (no syncytia), the antigen content decreases from 2.0 ng/ml down to 0.1 ng/ml.

4. On the cell level, all the above biologically active concentrations are nontoxic for AZT and AC-1 and AC-4 preparations as well.

5. In tests with animal in case of intramedullary injection of AZT in nonlinear white mice in a dose of 10 mg/kg of weight, 50% of animals die. At the same time, intramedullary injection of AC-1 and AC-4 preparations in a dose of 50 mg/kg (5 times as high) produced no lethal effect on animals.

Thus, AC-1 and AC-4 preparations are at least five times less toxic than AZT.

Since the bioactive materials of the present invention are much less toxic than AZT, they can be utilized in larger doses for the inhibition of HIV. For example, while AZT is employed for oral administration in capsule form containing 100 mg per unit dose, larger amounts of the material of the present invention can be used in single dose forms for oral administration in amounts up to 500 mg and higher, and preferably 50 to 500 mg.

As previously indicated, the pharmaceutical compositions containing the bioactive material and a pharmaceutically acceptable carrier can be formulated by methods known in the art. A wide variety of carriers can be used and include, but are not limited to, inert materials such as cornstarch, magnesium stearate, microcrystalline cellulose, sodium starch glycolate and the like. The concentration of the bioactive material in the pharmaceutical compositions can vary depending upon the dosage required, frequency of administration and the age, weight and condition of the patient or host to whom the composition is administered. If desired, the pharmaceutical compositions can contain one or more other ingredients which are active against the AIDS virus and include compounds such as AZT, DDI and the like.

As indicated above, the bioactive materials of the present invention are useful for inhibiting the growth of viruses which are susceptible to treatment by such materials. The bioactive materials of the present invention inhibit the interaction of gp 120 virus protein with CD4 receptor on cellular surfaces of a host and hence are useful for inhibiting the growth of the AIDS virus.

In another embodiment of the invention, compositions containing the DNA-sodium salt have application in the cosmetic field. The DNA-sodium salt compositions have been successfully used as components in creams and lotions. The compositions are useful for preventing aging pigmentation of the skin, removing blackheads, pimples, scars, healing cuts and burns, reducing inflammation and acting as a rejuvenating cream to make the skin feel soft and elastic. It has also been observed that the DNA-sodium salt is useful for strengthening and restoring hair. It can also be used as a mouthwash or in toothpaste since it has a strong antiperiodontosis effect. The DNA-sodium salt can be used in formulations for the aforementioned uses, as a powder, solution or in gel form.

A typical cosmetic preparations containing NPD-A was prepared for smoothing aging skin. The data showing the results on the general pharmacological activeness and toxicological characteristics are set out in Examples 12 and 13 below.

The composition is prepared for topical application having from about 0.05 to about 10.0 per cent of the active ingredient and preferably from about 0.3 to about 0.8 per cent by weight of the cosmetic preparation.

EXAMPLE 12

A cosmetic preparation for topical application for the treatment of aging skin was prepared by the following materials in by weight:

| | |
|---|---|
| DNA-sodium | 0.36 |
| rose water | 3.5 |
| $C_{15}$—$C_{20}$ hydrocarbons | 2.0 |
| dehydrated lanoline | 1.0 |
| vodlan-60 | 1.0 |
| glycerin monostearate | 2.0 |
| emulsion waxes | 2.0 |
| distilled monoglycerides | 2.0 |
| butylstearate | 5.0 |
| sodium laurylsulfate | 0.4 |
| olive oil | 10.0 |
| perfume oil | 6.0 |
| paraoxybenzol acid methyl ether | 0.5 |
| fragrance | 0.6 |
| balance | distilled water |

EXAMPLE 13

The cosmetic composition prepared in Example 12 was administered to 15 women varying in age from 30 to 56 years. The composition was applied to the face and hand skin 2 times daily for days by rubbing into the skin with circular hand movements.

The resilience of the skin was studied among 8 of the test subjects with the help of an experimental device with a piezoelectric sensitive element designed in the Institute of Biophysics of Russian Academy of Sciences. After the first application, skin resilience was measured in symmetric points of the face skin (above the eyebrow, on the cheekbone, near the corner of the mouth, and under the lower jaw) before and 5 to 10 minutes after the application. The composition rapidly and effectively entered the skin after its application and the average values of skin resilience after the application remained practically unchanged.

All of the patients noted the sensation of skin "freshness" during the course of treatment and by the time it was finished, face skin became smooth and its nutrition was promoted. Average skin elasticity enlarged by 15–20%.

There was no evidence of skin irritation, allergic reactions or any other side effects on any of the patients.

In addition to the use of the DNA-sodium salts in formulations for the treatment of skin for cosmetic purposes, they are also useful, as previously indicated, formulations for their grooming, toothpaste, mouthwash and the like. In such formulations the DNA-sodium salt can be present in concentrations of from about 0.1 to about 1.0 per cent by weight of the formulation. The DNA-sodium salts can be used, as the sole active ingredient in such formulations or in combination with other active components.

The formulation base for the various products is comprised of ingredients known in the art for such applications the only requirement being that none of the ingredients contained therein, adversely affect, or are adversely affected by the DNA-sodium salt.

Although the invention has been illustrated by the preceding examples, it is not to be construed as being limited to the materials employed therein, but rather, the invention is directed to the generic area a herein after disclosed. Various modifications and embodiments thereof can be made without departing from the spirit or scope thereof.

What is claimed is:

1. A cosmetic formulation for the treatment of skin comprised of a cosmetic base and a DNA-sodium salt composition, obtained by extracting DNA with a sodium chloride solution, from the reproductive cells of a member selected from the group consisting of sturgeon, seruga and beluga milt.

2. The cosmetic formulation of claim 1 wherein the DNA-sodium salt composition is comprised of:
    (a) not less than 80 percent by weight of a DNA-sodium salt having the following characteristics:
        molecular weight $270$–$500 \times 10^3$ Daltons,
    (b) not more than 1 percent protein by weight, and
    (c) not more than 17 percent moisture by weight.

3. The cosmetic formulation of claim 2 wherein the DNA sodium salt is obtained from seruga milt.

4. A cosmetic formulation of claim 2 wherein the DNA-sodium salt has a nucleotide composition in the mole percent of:

| | |
|---|---|
| adenine | 29.0 |
| thymine | 27.0 |
| guanine | 22.0 |
| cytosine | 20.0 |

5. The cosmetic formulation of claim 1 wherein the DNA-sodium salt is obtained from sturgeon milt.

6. The cosmetic formulation of claim 1 wherein the DNA-sodium salt is obtained from beluga milt.

7. The cosmetic formulation of claim 1 which is in the form of a gel.

* * * * *